US011317887B2

(12) United States Patent
Boll et al.

(10) Patent No.: US 11,317,887 B2
(45) Date of Patent: May 3, 2022

(54) COMPUTED TOMOGRAPHY RECONSTRUCTION OF MOVING BODIES

(71) Applicant: 3SHAPE A/S, Copenhagen K (DK)

(72) Inventors: Morten Boll, Espergærde (DK); Sami Brandt, Bunkeflostrand (SE); Thomas Sangild Sørensen, Aarhus C (DK)

(*) Notice: Subject to any disclaimer, the term of this patent is extended or adjusted under 35 U.S.C. 154(b) by 29 days.

(21) Appl. No.: 16/762,718

(22) PCT Filed: Nov. 12, 2018

(86) PCT No.: PCT/EP2018/080906
§ 371 (c)(1),
(2) Date: May 8, 2020

(87) PCT Pub. No.: WO2019/092236
PCT Pub. Date: May 16, 2019

(65) Prior Publication Data
US 2021/0169437 A1   Jun. 10, 2021

(30) Foreign Application Priority Data

Nov. 10, 2017   (DK) .............................. PA201770843

(51) Int. Cl.
A61B 6/00   (2006.01)
A61B 6/02   (2006.01)
(Continued)

(52) U.S. Cl.
CPC .............. *A61B 6/547* (2013.01); *A61B 6/025* (2013.01); *A61B 6/032* (2013.01); *A61B 6/0492* (2013.01);
(Continued)

(58) Field of Classification Search
CPC ........ A61B 6/14; A61B 5/1114; A61C 19/045
See application file for complete search history.

(56) References Cited

U.S. PATENT DOCUMENTS 8,320,612 B2   11/2012   Knobel et al.
8,808,000 B2   8/2014    Salcedo et al.
(Continued)

FOREIGN PATENT DOCUMENTS

WO   2011090775 A2   7/2011
WO   2013166299 A1   11/2013
(Continued)

OTHER PUBLICATIONS

International Search Report (PCT/ISA/210) dated Feb. 12, 2019, by the European Patent Office as the International Searching Authority for International Application No. PCT/SE2017/051202.
(Continued)

*Primary Examiner* — Dani Fox
(74) *Attorney, Agent, or Firm* — Buchanan Ingersoll & Rooney PC

(57) ABSTRACT

A method for reconstructing at least a first and a second independently moving body from one 3D tomography scan includes performing a movement of the first body relative to the second body, obtaining the movement, obtaining a 3D tomography scan of the first body and the second body during the movement, and reconstructing a first 3D model of the first body and a second 3D model of the second body by applying the recorded movement to the 3D tomography scan. This has the effect that reconstruction of several 3D tomography scanned bodies is possible during motion of the scanned bodies.

17 Claims, 7 Drawing Sheets

(51) Int. Cl.
 *A61B 6/03* (2006.01)
 *A61B 6/04* (2006.01)
 *A61B 6/14* (2006.01)

(52) U.S. Cl.
 CPC .............. *A61B 6/14* (2013.01); *A61B 6/4452* (2013.01); *A61B 6/466* (2013.01)

(56) References Cited

U.S. PATENT DOCUMENTS

| | | |
|---|---|---|
| 9,554,872 B2 | 1/2017 | Koubi et al. |
| 2005/0070782 A1 | 3/2005 | Brodkin |
| 2007/0190481 A1 | 8/2007 | Schmitt |
| 2007/0190492 A1 | 8/2007 | Schmitt |
| 2009/0076371 A1 | 3/2009 | Lang et al. |
| 2012/0015316 A1 | 1/2012 | Sachdeva et al. |
| 2013/0316298 A1 | 11/2013 | Ikegami et al. |
| 2014/0294273 A1 | 10/2014 | Jaisson |
| 2015/0202022 A1 | 7/2015 | Branch et al. |
| 2016/0262711 A1* | 9/2016 | Nyholm ................ A61B 5/1114 |
| 2017/0000430 A1 | 1/2017 | Lu et al. |
| 2017/0143445 A1 | 5/2017 | Abkai |

FOREIGN PATENT DOCUMENTS

| | | |
|---|---|---|
| WO | 2016139347 A1 | 9/2016 |
| WO | 2016142943 A1 | 9/2016 |
| WO | 2016196592 A1 | 12/2016 |

OTHER PUBLICATIONS

Written Opinion (PCT/ISA/237) dated Feb. 12, 2019, by the European Patent Office as the International Searching Authority for International Application No. PCT/SE2017/051202.

C. Epstein et al., "Introduction to the Mathematics of Medical Imaging", Second Edition, Siam, 2008, ISBN: 978-0898716430. (7 pages).

J. Hsieh, "Computed Tomography; Principles, Design, Artifacts, and Recent Advances", Second Edition, SPIE, 2015, ISBN: 978-1628418255. (6 pages).

* cited by examiner

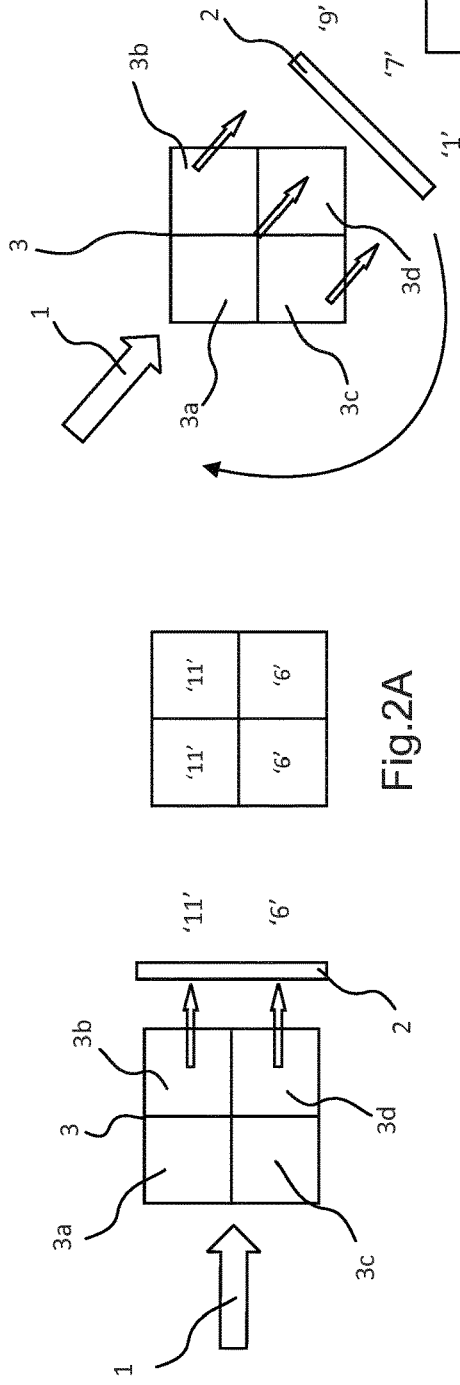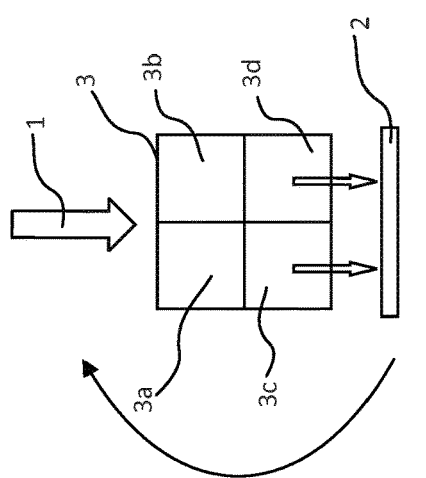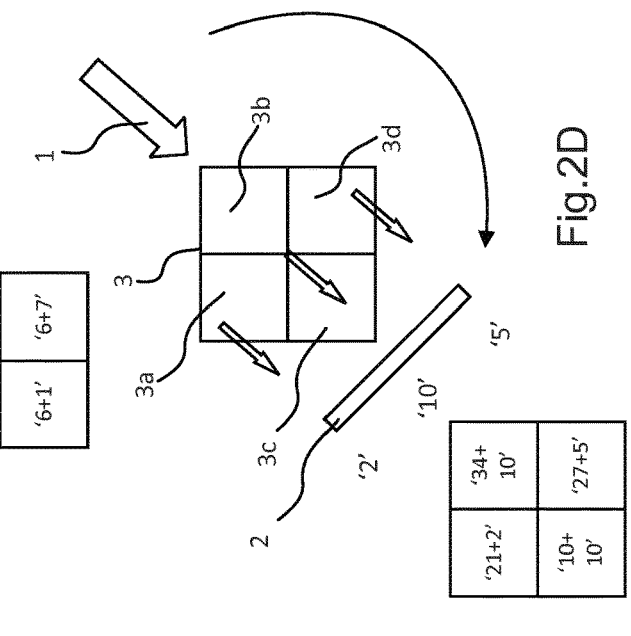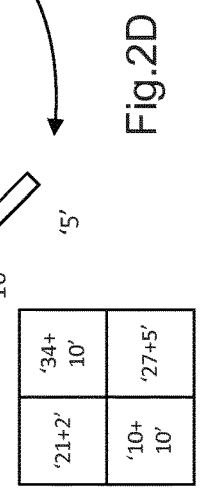

COMPUTED TOMOGRAPHY RECONSTRUCTION OF MOVING BODIES

FIELD

Disclosed herein is a system and a method for reconstructing at least two independently moving bodies from a single CT scan. In particular, the disclosure relates to reconstructing the two bodies from the CT scan data based on their relative movement and in addition simultaneously obtain said relative movement between the two bodies, which can be played back for later use. Any additional measurements of movements of the bodies, prior or subsequent to the scan, with or without ionizing radiation, can be used to obtain 3D volume data of each body in any configuration of movements between the two bodies.

BACKGROUND

Radiographic imaging (such as x-ray imaging) is a commonly used technique for sub tissue imaging. Single exposure images are used to provide a medical practitioner with an indication of the sub tissue situation and provide a first diagnose evaluation.

However, such single exposure images have no depth information and sometimes it is difficult to discern details without more depth information.

CT (computed or computerized tomography) scanners have subsequently been developed and are commonly used in todays medical practice. CT scanners makes used of several single exposure images to build a 3D volume of voxels, which will represent a 3D model of the scanned body. Since these images are taken in a sequential order there is a time frame within which the scanner takes the necessary number of images to build up the 3D model. Any motion within this time frame results in blurring in the reconstructed 3D model.

In order to reduce such motion many CT scanner includes fixation means of different types and although the accommodate the problem to some extent movement may still be caused and the fixation may also cause an uncomfortable and claustrophobic experience for the patient.

Another way to prevent motion blur is described in applicants published application WO2016139347A1 where motion of the patient is detected and subsequently used to correct for motion during reconstruction of the 3D model.

Where WO2016139347 relates to compensate for movement of only one moving body, during applicants further work with such motion compensating reconstruction, it has surprisingly been found that it is actually possible to reconstruct separately moving bodies from a single CT scan.

In particular, it has actually shown that by providing movement between at least two bodies during a CT scan it is actually possible to extract the models of the bodies during reconstruction of the CT scan.

Accordingly, where a lot of effort has previously been put into reducing and eliminating movement, it is actually a prerequisite for the current invention that movement is present during CT scanning.

The present invention does not only allow the bodies to be derived during reconstruction. It further allows to identify how the bodies move naturally relative to each other without having to apply any post-processing steps. This become particularly relevant in applications where important information may be derived from the models of the bodies, and in particular the movement of the bodies relative to each others, such as the chewing motion of the mandible and the maxilla, joint movement of extremities such as fingers, arms, feet, legs etc. Other non-medical applications of the invention may also be anticipated such as mechanical joint movement.

SUMMARY

In one aspect there is disclosed a method for reconstructing at least a first and a second independently moving body from one 3D tomography scan, comprising:
  performing a movement of the first body relative to the second body,
  obtaining the movement,
  obtaining a 3D tomography scan of the first body and the second body during the movement, and
  reconstructing a first 3D model of the first body and a second 3D model of the second body by applying the obtained movement to the 3D tomography scan.

This has the effect that reconstruction of several 3D tomography scanned bodies is possible during motion of the scanned bodies. Accordingly, the problem of scanning several bodies moving relative to each other can be solved in this manner.

3D tomography should be understood as a sub-tissue digital imaging technique from which a 3D model can be established. In particular, 3D tomography covers MR (magnetic resonance) scanning and CT (computed tomography) scanning within the context of this disclosure.

In the current disclosure there is focused on CT scanning, although the principles should be applicable to MR scanning as well. The reference to CT (computer tomography scanning) should be read broadly and understood as any type of radiographic imaging that is handled digitally in order to provide a 3D model of the scanned object. According, as examples, CBCT (cone beam computed tomography) imaging, FBCT (fan beam computed tomography) and PET (positron emission tomography) are all considered a type of CT scanning.

The CT scan may be obtained in different ways. It may be recorded directly by performing a single CT scan data acquisition or it can for example be obtained by loading it via an external source, e.g. downloading it from a cloud service or receive it by email as a data file.

Within the present disclosure it is discussed how to reconstruct a 3D model. The 3D model is typically a volumetric representation of scanned body, e.g. the 3D model is represented by voxels. Furthermore, the term "reconstructing" is commonly used in the art when building a volumetric representation, which is typically done from information derived from 2D images taken of the body during scanning. Accordingly, although it may in some cases be more appropriate to use the term "constructing" since there is no volumetric representation of the scanned body present before the scan the term "reconstructing" is the term preferably used in the art and understood by the person skilled in the art.

It should also be understood that the term "body" or "bodies" is used to refer to a part that is subject to being scanned and for which a 3D reconstruction is to be provided. Such a "body" can within the medical area be a part of the human body such as the jaw or part of a jaw or skull. It can be an extremity such as part of the limbs between respective joints and in particular arms, legs, hands, finger, feet and toes. The term can also refer to a part of an animal, and it can even refer to machined parts that is to be inspected by a CT scan.

Also, "independently moving" should be understood as two parts that are free to move in at least one dimension relative to each other. E.g. the finger of a human (except for the thumb) is formed of three bodies (the distal, middle and proximal phalanx bones) that may move independently relative to each other due to the two joints separating these. This movement is still considered independent since they can move relative to each other in one plane.

The movement can be obtained in different ways. It can be determined directly by recording the movement or it could be obtained by loading it from an external source, e.g. downloading it from a cloud service or receive it by email as a data file.

In order to determine the movement of a body the method in some embodiments further comprises recording the movement by attaching an at least first scan reference to the first body and tracking the at least first scan reference during the movement. A scan reference is an element that is detectable by the tracking system. For example, and as discussed further below, an optical tracking system (e.g. cameras) may use dot plates as scan references in order to track the movement of the body to which the scan reference is attached.

In one embodiment the method further comprises fixating the second body. In such cases there is no movement of the second body relative to the scanner and is thereby already arranged in the coordinate system defined by the scanner itself.

However, in an alternative embodiment the method may comprise attaching a second scan reference to the second body and tracking the at least first scan reference during the movement.

More than two independently moving bodies may be tracked and reconstructed using the method disclosed herein. Accordingly, in one embodiment the method comprises that a third or more bodies are present and a respective third or more scan references are attached to each third or more bodies.

For example when scanning a finger, separate scan references are attached to the distal, middle and proximal phalange and the movement of each phalange is then tracked during the CT scan.

Different methods can be used to track the movement of the respective bodies. One embodiment wherein movement is recorded can be by using an optical system comprising cameras. In principle one camera can be sufficient in for example tracking a dot plate. A dot plate is a plate whereon an optical recognizable pattern in the shape of dots are provided, from which the position of the scan reference can be unambiguously derived. Although use in one camera may in some cases be sufficient the precision will typically be low perpendicular to the camera plane. For increased accuracy more cameras can be used. Accordingly, in one embodiment at least three cameras are used for detecting the first, second, third or more scan references. The movement is then recorded by the cameras, e.g. in a video stream, from which the position of the scan reference may be derived at individual time frames, which subsequently is correlated with the time frames of the CT scan.

By using three cameras the movement can be detected in all dimensions. Of course, the scan references should be optimized for optical tracking with distinguishing optical tracker elements provide therein.

In another embodiment, an ultrasound tracking system may be provided where the scan references are detected by ultrasound. In some embodiments, movement sensor(s), accelerometers or a combination of the two may be employed to record the movement of the two bodies during the CT scan.

It could even in some situation to track the body directly and without a scan reference if the body has specific characterizing features that enables tracking. This could for example be facial features, skin features such as fingerprints, or shapes defined by the bodies to be scanned.

In order to apply the movement data to the method as described herein, the movement is in one embodiment digitized into a movement data file describing the movement in a resolution (format) compatible to the resolution of the CT scan.

In one embodiment the movement data from the movement data file is used in a reconstruction algorithm applied to the CT scan for reconstructing the at least first and second body.

To facilitate the reconstruction of the CT scan the at least first and second body are in one embodiment considered rigidly moving bodies and the movement of each body are represented by at least a first and a second transformation matrix.

The attenuation of each rigid body can in another embodiment be described in a superposition of at least two linear models, each describing the attenuation of the respective at least first and second body. The term "attenuation" refers to how easily a radiographic beam (x-ray) passes through a body. As discussed later a high "attenuation coefficient" means that the radiographic beam is quickly weakened/absorbed (attenuated) as it passes through the body. As will be further discussed herein the scanned bodies are typically volumetric reconstructed and represented by voxels. Typically, the reconstruction is established by evaluating the attenuation coefficient of each voxel and by knowing the attenuation coefficient of e.g. skin, bone, and enamel it is possible to tell which voxel is skin, bone and enamel respectively.

One embodiment for solving the superposition of the at least two linear models can be to apply a respective at least first and second transformation matrix thereto.

The superposition of the at least two linear models can be solved iteratively or non-iteratively.

Another aspect disclosed herein a method for obtaining specific relative movement between at least a first and a second independently moving body, which has been reconstructed from one CT scan acquisition as disclosed herein is provided. The method for obtaining specific relative movement comprises:

performing a post movement of the first body relative to the second body after the CT data acquisition has been perform, and obtaining the post movement.

In particular in embodiments where an at least first scan reference is attached to the body and tracked during the CT scan acquisition as previously described the at least first scan reference is also used for obtaining the post movement by tracking and recording the movement of the first scan reference.

This has the advantage that even after the CT system is turned off in order to prevent further radiation exposure, the tracking system can proceed to track different motion patterns which can be directly applied to the reconstructed models since they are derived from within the same setup, and thus inherently placed in a common coordinate system.

For example when the first and second body are patient extremities the doctor or dentist can ask the patient to move them as they desire during CT acquisition where the doctor needs to be shielded from the patient. Afterwards, the doctor can join the patient and in detail instruct the patient to perform specific motion patterns without having to be concerned about radiation.

BRIEF DESCRIPTION OF THE DRAWINGS

The above and/or additional objects, features and advantages of the present invention, will be further described by the following illustrative and non-limiting detailed description of embodiments of the present invention, with reference to the appended drawing(s), wherein:

FIG. 2A-2E shows a very simple diagram of how to reconstruct voxel attenuation information based on a CT scan sequence as known in the art.

DETAILED DESCRIPTION

In the following description, reference is made to the accompanying figures, which show by way of illustration how the invention may be practiced.

1. Embodiments for Scanner Setups

Figure 1:
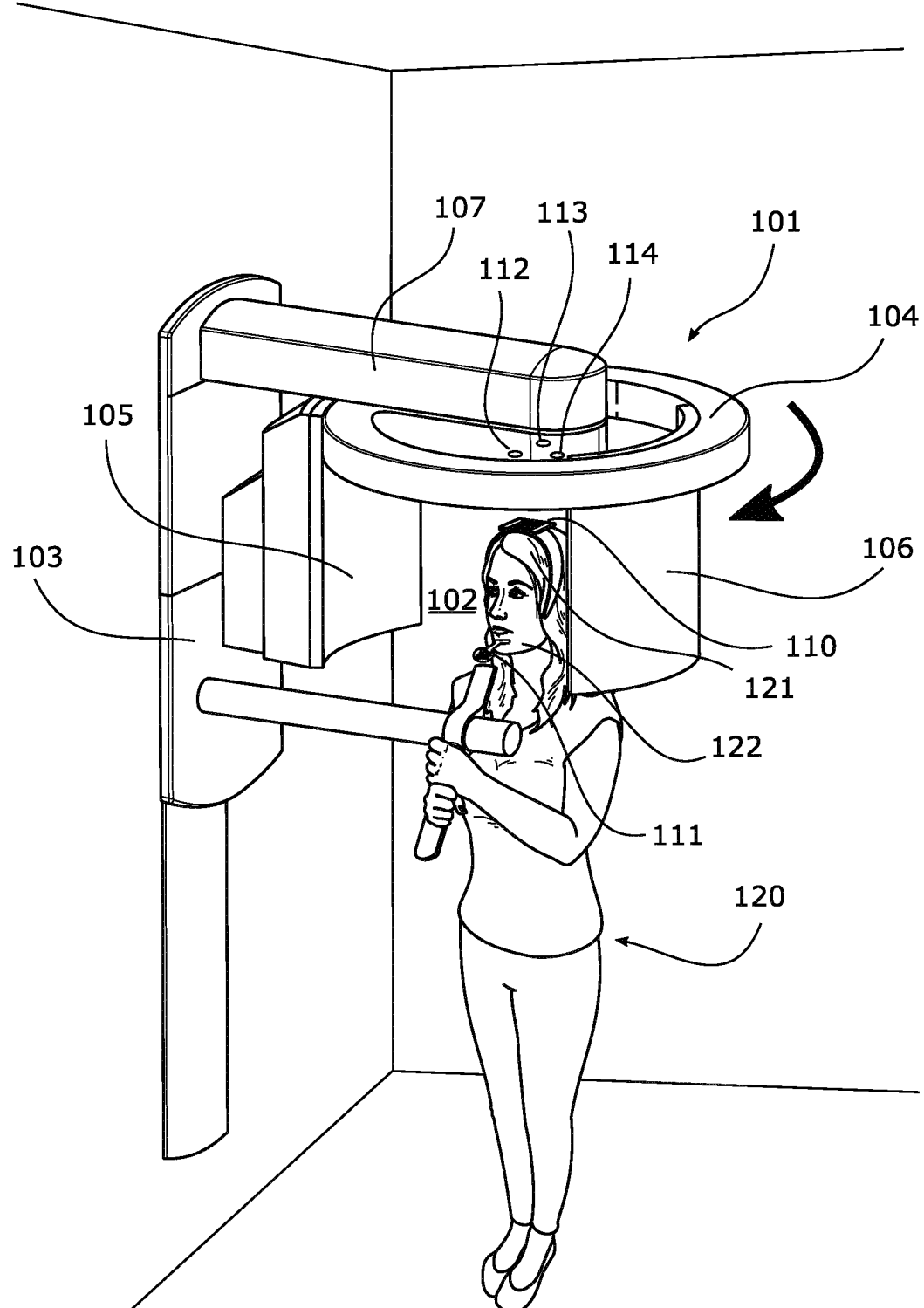
FIG. 1 shows a CBCT scanner system configuration as disclosed herein.

FIG. 1 illustrates an embodiment of a scanning setup according to the invention.

A patient 120 is placed in the scanning volume 102 of a CBCT scanner 101. The CBCT scanner 101 is formed of a scanner body 103 from which a scanner arm extends. The scanner arm 107 supports a rotating scanner gantry 104. The gantry is formed of a radiation source 105 and a radiation sensor 106. During rotation the radiation source and sensor rotates and the volume within the source and sensor is the scanning volume.

A maxilla scan plate 110 is placed on top 121 of the patient's head. Accordingly, the maxilla scan plate will follow the movement corresponding to the maxilla (upper jaw) of the patient.

A mandible scan plate 11 is placed on the chin 122 of the patient's head. Accordingly, the mandible scan plate will follow the movement corresponding to the mandible (lower jaw) of the patient.

The scan plates are provided with optical reference markers that with high precision can be detected by an optical detection system. In the current embodiment the optical detection system is formed by three cameras 112, 113, 114 placed in the top of the gantry. As the cameras continuously records the optical reference markers it is possible to detect position, and over time the change in position resulting in the movement of the respective scan plates.

Accordingly, the CBCT scanner scans the patient by rotating the gantry and exposing the patient at known intervals and positions of the gantry. At the same time a tracking system, comprising the three cameras and the two scan plates, detects the motion of the maxilla and the mandible during the CBCT scan. This data can subsequently be used to reconstruct independent 3D models of the maxilla and the mandible without having to do any post segmenting of the scan. In addition since the motion has been recorded, the actual motion can be used subsequently by the doctor to analyse the natural jaw motion of the patient.

Subsequent to the CBCT scan the radiographic source can be turned off while still keeping the tracking system operable. This enables further patient specific motion to be applied to the 3D models of the maxilla and the mandible without exposing the patient to further unnecessary radiation.

The following sections will discuss the basic theories behind volumetric reconstruction, how it can be expanded to compensate for movement by using the registered motion of a moving body during scanning.

Finally it will be disclosed in more detailed how this can further be expanded to allow for reconstruction of multiple moving bodies based on one CT/CBCT scan.

2.1 Theoretical Background for Volumetric Reconstruction

The fundamental principles of computed tomography (CT) are well described in the literature, see e.g. [1-2]. Here we review merely a small two-dimensional (2D) schoolbook example with a point detector for simplicity. The principles however generalize to further image dimensions and different detector types (e.g. curved and flat 2D/3D detectors).

The tomographic imaging is a linear inverse problem arising from the linear, forward model p=Aµ where µ is a vector of attenuation coefficients (pixel/voxel values), p is a vector of attenuation measurements (detector pixel values) of the projected image, and A is a matrix describing a mathematical projection rule, i.e. how projected, 2D pixel measurements depend on the spatial attenuation coefficients. The inverse problem in tomographic imaging corresponds to solving for the vector of attenuation coefficient µ given the measurements p under assumptions of the projection geometry in the form of the projection model A. It should be understood that µ is a vector of attenuation coefficients. However, seeing that the 3D volume of voxels/3D model of the scanned body is made up of attenuated voxel elements it can also be said that µ represents an image/model of the scanned object/body in a mathematical representation.

By the way of a basic example below, we refer to general common knowledge such as discussed in [2].

Figure 6:
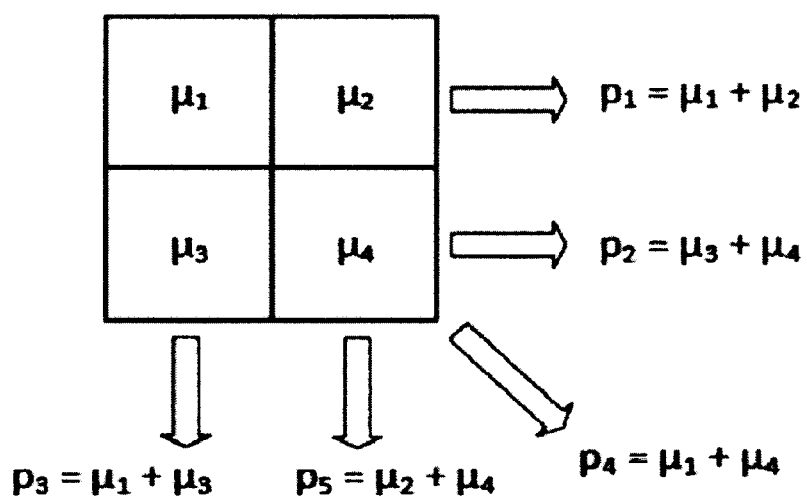
FIG. 6 includes Diagram 1 and Diagram 2 which illustrate x-ray point measurements $p_1$, $p_2$, $p_3$, $p_4$, and $p_5$.

The 2D image to be reconstructed consists of four pixels, $\mu_1$, $\mu_2$, $\mu_3$, $\mu_4$. Five x-ray point measurements, $p_1$, $p_2$, $p_3$, $p_4$, $p_5$, were made, as shown in Diagrams 1 and 2 in FIG. 6. Each measurement, $p_i$, corresponds to a line integral of the attenuation through the image at a given angle and offset. Utilizing basic "nearest neighbor" interpolation of the line integral computations (real life implementations would often use different interpolation schemes), each measurement captures the sum of two image elements. The setup gives rise a linear system of equations:

$$p_1 = \mu_1 + \mu_2 \qquad \text{Eq. 1a}$$

$$p_2 = \mu_3 + \mu_4 \qquad \text{Eq. 1b}$$

$$p_3 = \mu_1 + \mu_3 \qquad \text{Eq. 1c}$$

$$p_4 = \mu_1 + \mu_4 \qquad \text{Eq. 1d}$$

$$p_5 = \mu_2 + \mu_4 \qquad \text{Eq. 1e}$$

This system can be written in matrix/vector form as depicted in the rightmost image above.

Note that since $p_5=p_1+p_2-p_3$ the equations are not linearly independent. Any combination of four of the five equations containing $p_4$ is however linearly independent. The corresponding system of equations can be solved in a number of ways, e.g. by direct matrix inversion (for square, linearly independent systems), filtered backprojection, or iterative methods. For iterative reconstruction the problem is often rewritten as an optimization problem that finds the image µ' representing the scanned body which is most consistent with the acquired data, e.g.

$$\mu'=\mathrm{argmin}_\mu |A\mu-p|^2. \qquad \text{Eq. 2}$$

The vector norm |.| usually denotes the Euclidian $I_2$ norm but others are possible. To increase the robustness of the solution process and to suppress measurement errors, a regularization term, R, is often included in the optimization problem, e.g.:

$$\mu'=\mathrm{argmin}_\mu |A\mu-p|^2+|R\mu|^2. \qquad \text{Eq. 3}$$

To simplify the example we have used the squared $I_2$ norm for both vector norms. State-of-the-art reconstructions however often utilize other norms for one or both terms; examples include total variation regularization and compressed sensing based reconstruction.

2.2 Simple Practical Example of Volumetric Reconstruction

FIG. 2A-2E illustrates in a simple manner how the attenuation information of a voxel is determined as discussed above. FIG. 2A-2E are described in a simple 2D overview but it is well known how this is applied with actual CT scan data in order to reconstruct a 3D body.

A first radiographic image is taken in FIG. 2A where an x-ray 1 is transmitted from a source (not shown) onto a x-ray detector 2. The x-ray passes through a scan body 3 placed in a scan volume between the x-ray source and the x-ray detector 2. When passing through the scan body the x-ray is attenuated depending on the material it passes through. The scan body defines four voxels 3a, 3b, 3c and 3d. In order to reconstruct a 3D model of the scan body it is necessary to determine the attenuation, i.e. the radiation absorbed in each voxel, as will be described in the following.

The x-ray source and the x-ray detector are arranged opposite each other in a gantry and are arranged so that they can rotate on opposite sides around the scan volume.

Accordingly, as shown in FIG. 2A the x-ray will pass the scan object through voxels 3a, 3b and 3c, 3d respectively. Based on the incident radiation on the x-ray sensor it can be determined that the attenuation of the part of the x-ray passing through the top row, i.e voxel 3a and 3b, is '11' and the attenuation of the part of the x-ray passing through the bottom row, i.e. voxels 3c and 3d is '6'.

An array 10 can subsequently be construed with four elements 11a, 11b, 11c and 11d each representing the respective voxel 3a, 3b, 3c and 3d of the scan body. After the first medical image has been capture as described in respect to FIG. 2A the total attenuation of the upper row 3a and 3b is inserted in the upper array element 11a and 11b, which in this case is '11'. Similarly the total attenuation, which is '6', of the lower row 3c and 3d is inserted into matric elements 11c and 11d.

The x-ray source and the detector 2 is then rotated 45 degrees clockwise into the position shown in FIG. 2B.

In this setup the scanning body is exposed from a new angle, resulting in detected attenuation of '9' for the part of the x-ray passing through voxel 3b, an attenuation of '7' for voxels 3a and 3d and an attenuation of '1' for voxel 11c. These values are added the current value from FIG. 2A in the corresponding elements in the array, i.e. The value '9' is added to the value '11' in element 11b, the value '7' is added to the values '11' and '6' in elements 11a and 11d respectively and the value '1' is added to the value '6' in element 11c.

The x-ray source and the x-ray detector is then rotated 45 degrees again as shown in FIG. 2C and the process repeated by exposing the scanning body through the column 3a, 3c and 3b, 3d and adding the detected attenuation values correspondingly to the matric element.

A final rotation of 45 degrees is then done as shown in FIG. 2D adding the corresponding values to the corresponding array element.

Figure 2E:
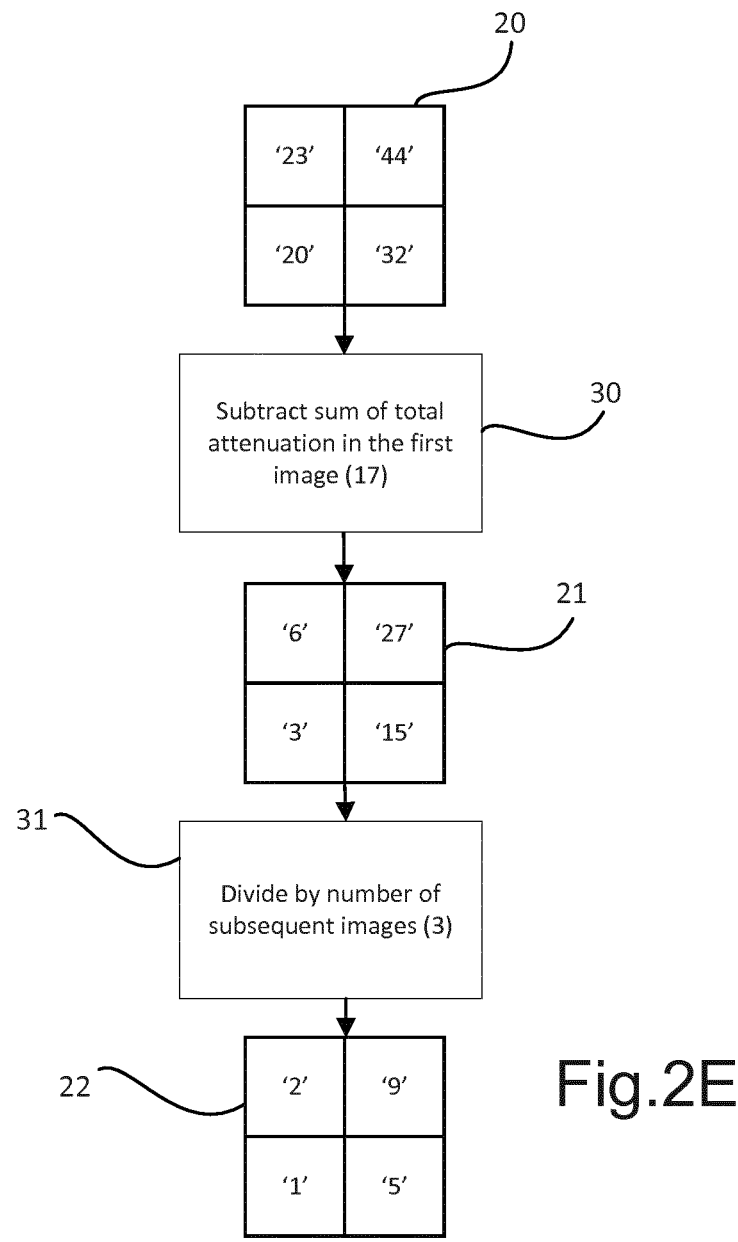

The final result of all the exposure steps in the current example can be seen in the array 20 in FIG. 2E. The data is then postprocessed in a first step 30 where the sum of the total attenuation (11+6=17) of the first medical image is subtracted from all the array elements resulting in an intermediate array 21.

In a final step 31 each array cell is divided by the number of medical images minus one, i.e. 4−1=3, which results in the final array 22.

The value of each array element 11a, 11b, 11c and 11d in the final array 22 corresponds to the actual attenuation value of respective voxels 3a ('2'), 3b ('9'), 3c ('1') and 3d ('5').

The current process is well known and can be expanded to include a much higher number of voxels and number of medical images.

However, in practice the current process is very sensitive to movement of the scanning body. In particular, since the scanning body often is a human part this is a very common issue and too much movement will compromise the detail of the CT image and in some cases even make it so blurred that it cannot be used.

Since every CT scan exposes a patient to a radiologic dose it is critical that non-useable scans are avoided.

In order to minimise this problem it is common to fixate the patient in order to avoid movement. This can however be difficult since it requires different physical fixation means that does not fit everyone in general and can also cause claustrophobic situations where the patient is fixed in a big CT or CBCT scanner that rotates around his or hers body.

However, as discussed above another solution have recently been proposed in published application WO2016139347A1 where the movement of the scanning body is registered and then subsequently used to compensate the attenuation values during reconstruction.

3.1 Theoretical Background of Reconstruction with Motion Compensation

The reconstruction problem of solving µ assuming the forward model $$p=A\mu \qquad \text{Eq. 4}$$

can be adapted to a scenario in which motion of the object, represented by the vector attenuation coefficients µ, occurs during data acquisition. If e.g. a rigid transformation, $T_i$, is captured by the scanning system according to each measurement $p_i$, then the matrix A can be defined, by construction, to include the transformations $T_i$; each transformation matrix $T_i$ is incorporated into row i in matrix A. Similar to the conventional (stationary) reconstruction problem, a number of well-known approaches, iterative or non-iterative, can be applied to reconstruct the represented image µ.

3.2 Simple Practical Example of Reconstruction with Motion Compensation

Figure 3B:
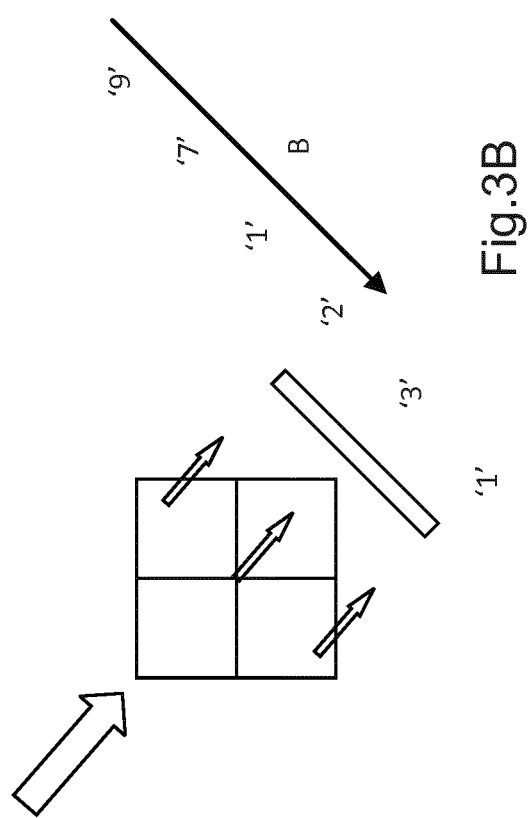
FIG. 3A-3B illustrates how motion information can be used to reconstruct voxel attenuation information for a body which has moved according to the movement information.
Figure 3A:
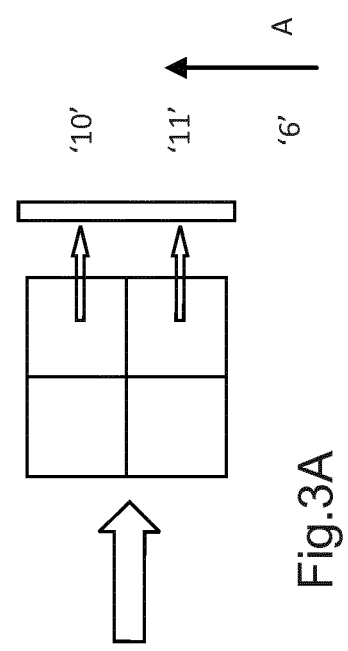

In FIGS. 3A and 3B an example embodiment of such motion compensation is illustrated.

FIG. 3A corresponds to the imaging step in FIG. 2B. Due to movement of the body the sensor 2 detects row attenuation values of '10' and '11' instead of '11' and '6'. However, with the movement of the scanning body determined and linked to the scanning time of the CT/CBCT system it is possible to compensate for this by shifting the detected attenuation values according to the movement as indicated by the arrow 'A'. Of course, this requires a sensor larger than the desired scan volume in order to record the data that may be within the range of movement.

Similarly, it can be seen in FIG. 3B that motion detected by a motion tracking system is used to shift the detected attenuation values along the arrow 'B'.

Basically this provides a clear image of the element that performs the same motion as the movement detected by the motion tracking system. In other words it can viewed as the element is segmented out of the recorded CBCT data.

It has subsequently shown that if there are two independently moving elements, e.g. the maxilla and the mandible of a person, and the movement of each such element is recorded and referenced to the volume of a CBCT scanner it is possible to derive the digital representation of each of the elements by using the respective recorded movement while reconstructing the data as described above in FIGS. 2A-2E and FIGS. 3A and 3B.

4.1 Theoretical Background for Reconstruction of Multiple Individually Moving Bodies In the case of multiple rigid objects, the attenuation of each rigid component is described by a separate linear model. For simplicity, if there are two rigid components, the forward model can be written as $$p_1 = A_1 \mu_1, \text{ and} \qquad \text{Eq. 5}$$

$$p_2 = A_2 \mu_2. \qquad \text{Eq. 6}$$

Due to the linearity of the attenuation process, the total measured attenuation on the image plane hence is the superposition of the two attenuation components, Eq. 5 and Eq. 6, or, $$p_{tot} = A_1 \mu_1 + A_2 \mu_2. \qquad \text{Eq. 7}$$

The total forward model can be thus written as the joint linear model $$p_{tot} = A_{tot} \mu_{tot}, \qquad \text{Eq. 8}$$

where $A_{tot} = (A_1 A_2)$ and $$\mu_{tot} = \begin{pmatrix} \mu_1 \\ \mu_2 \end{pmatrix}.$$

In the inverse problem, one intends to solve $\mu_{tot}$ given the attenuation measurements $p_{tot}$ on the image plane and the projection models $A_1$ and $A_2$ of the rigid components.

In other words, now that for each measurement, $p_i$, that multiple (denoted j) transformation matrices are captured—each transformation corresponding to one sub-component of the represented image $\mu$. Denote these matrices $T_{i,j}$. The system of linear equations can then be written to reflect that we are reconstructing j individually "moving" images, represented by the vector attenuation coefficients $\mu_j$. The number of columns in matrix $A_{tot}$ now corresponds to the total number of elements in all represented images $\mu_j$ and each row i incorporates the transformation $T_{i,j}$. The matrix/vector formulation can then be written as $$A \begin{bmatrix} \vec{\mu_1} \\ \vec{\mu_2} \end{bmatrix} = \vec{p} \qquad \text{Eq. 8}$$

It should be understood that the mathematical background presented in Eq. 8 above quickly may result in a large and complex matrix which requires extensive processing capacity to solve. However, as known in the art, the above problem may be solved more expediently and without compromising with the accuracy of the result by for example solving it either iteratively or non-iteratively by using back-projection similarly to what has also been outlined above.

4.2 Simple Practical Example of Reconstruction of Multiple Individually Moving Bodies Thus, as an example, the shift along arrows 'A' and 'B' in FIGS. 3A and 3B respectively will be different and provide a different attenuation specific for that body for which the motion was recorded.

For example in FIG. 3A where the attenuation information is shifted one voxel based on a first set of movement data, which may be obtained relative to the first moving body, it may based on a second set of movement body be necessary to shift the attenuation information five voxels in the direction opposite the arrow 'A' in order to provide the correct attenuation information for the second moving body.

5. Test Setup

As illustrated in FIGS. 4A-4D a test setup 400 was established to determine the usability of the method described herein. A dental model of a maxilla 401 was provided with a first scan reference 402 and a lower jaw (from a pig) 403 was provided with a second scan reference 404.

The maxilla model 401 and the lower jaw 403 was then placed in a rig 405 that provided a linear movement along axis A-A between the model and the jaw.

A CBCT scan was then performed of the test setup where the model and the jaw was moving relative to each other along the axis A-A during scanning while an optical system formed of three cameras was detecting the movement of the first scan reference 402 and the second scan reference 404.

Figure 4D:
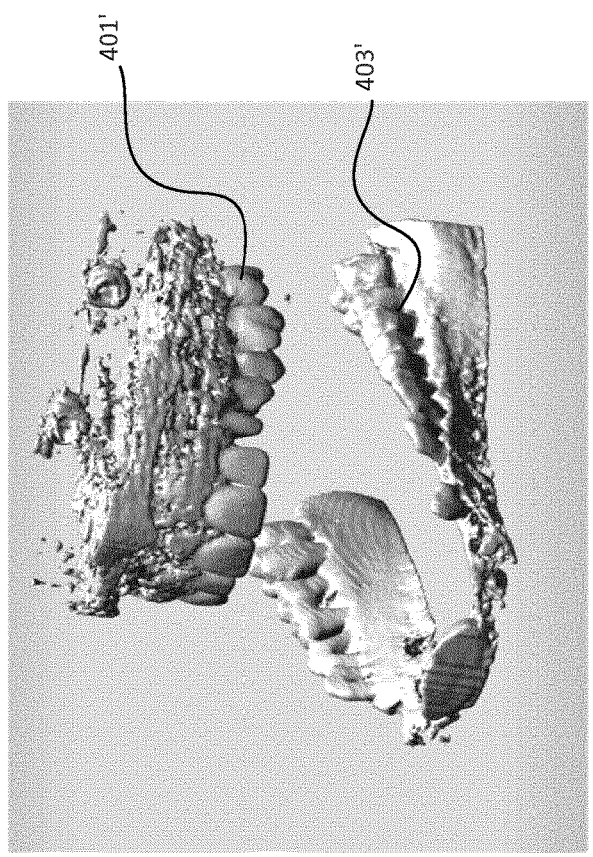
FIG. 4A-4D shows a test setup and scan results therefrom using the method as disclosed herein.
Figure 4C:
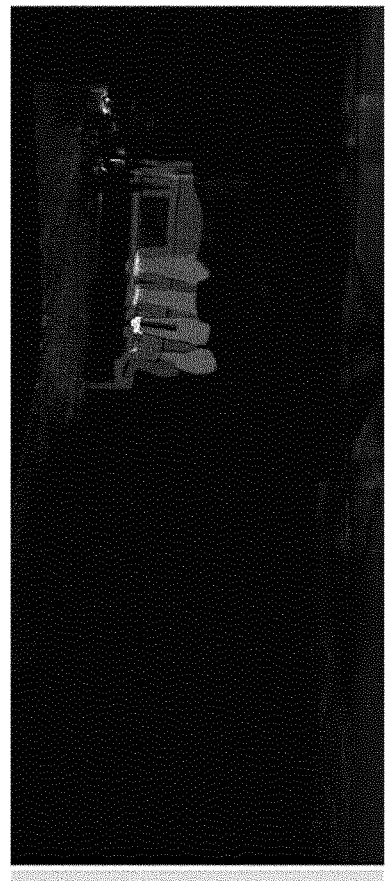
Figure 4A:
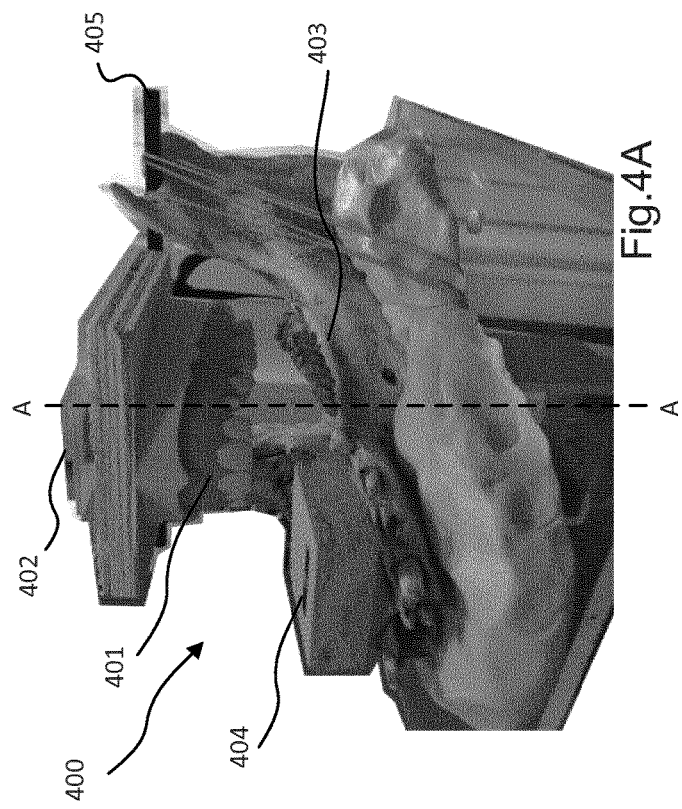
Figure 4B:
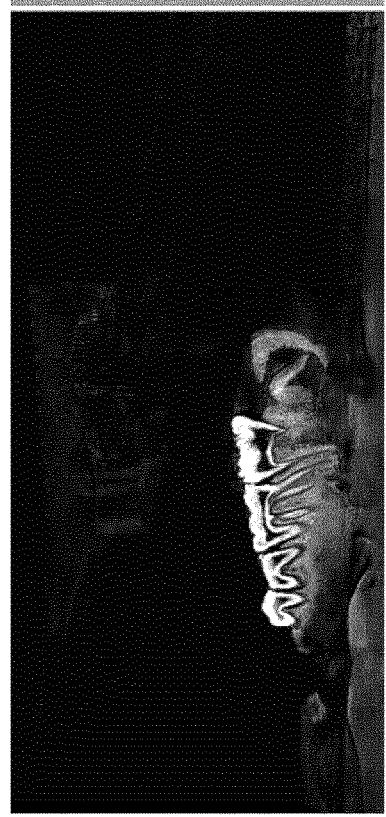

By using the principles set out in Eq. 8 above and solving it iteratively as suggested the image in FIG. 4B was reconstructed for lower jaw when feeding the formula with the movement of the second scan reference 404 and the image in FIG. 4C was reconstructed for the upper jaw by feeding the system with the movement of the first scan reference.

Basically, both the upper and lower jaw is reconstructed in the same process where the movement of both scan references are fed into the formula. The combined 3D reconstruction is shown in FIG. 4D where the 3D models of the upper jaw 401' and the lower jaw 403' are shown in relation to each other. Although not possible to see in the figures the complete reconstruction also contains the relative movement of the two jaws relative to each other, which can be important information to the dental practitioner, and which can be played back on the models shown in FIG. 4D.

Figure 5:
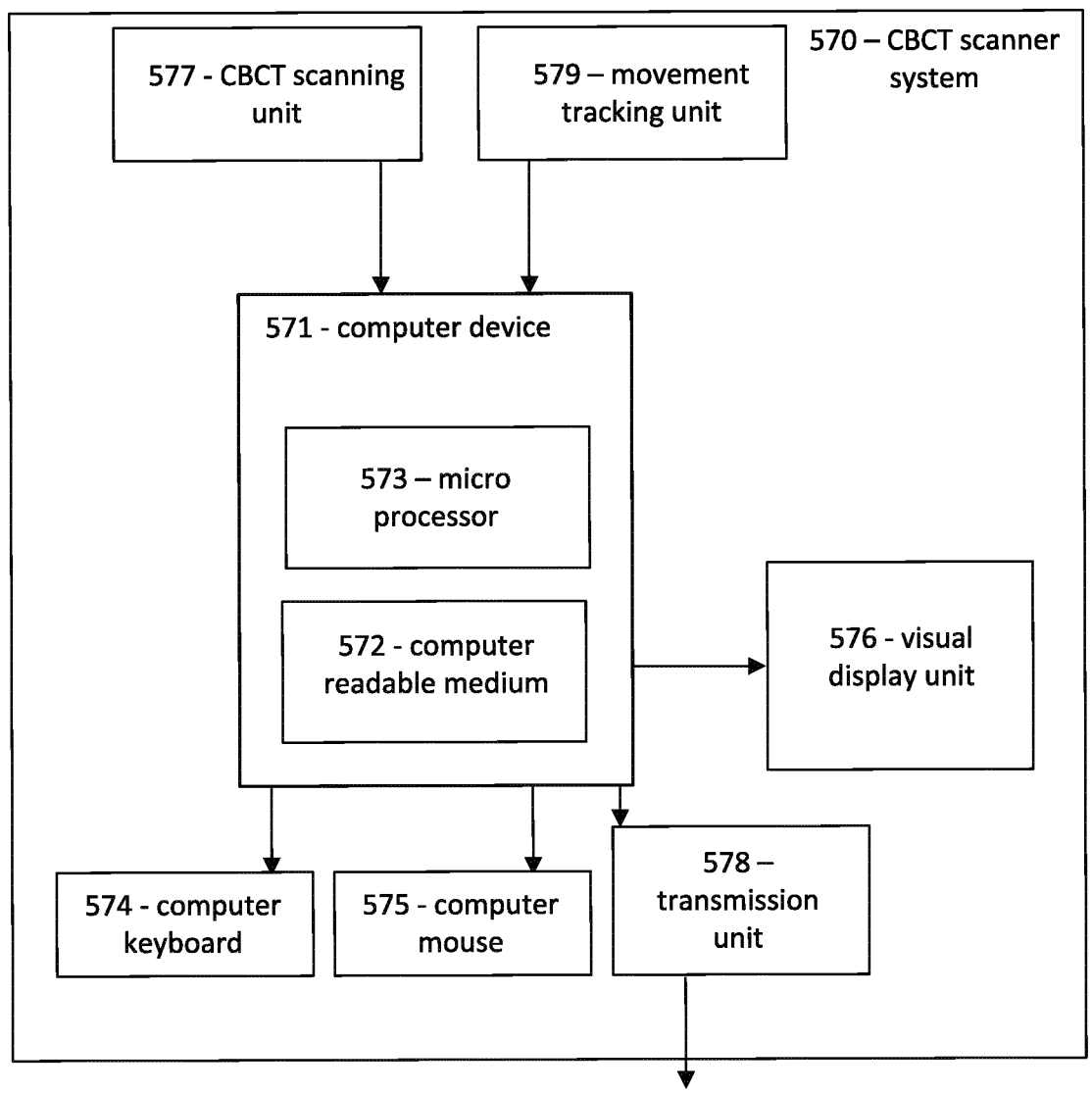
FIG. 5 shows a schematic view of a CBCT scanner system disclosed herein.

FIG. 5 shows a schematic of a CBCT scanner system 570. The system 570 comprises a computer device 571 comprising a computer readable medium 572 and a microprocessor 573. The system further comprises a visual display unit 576, a computer keyboard 574 and a computer mouse 575 for entering data and activating virtual buttons visualized on the visual display unit 576. The visual display unit 576 can be a computer screen.

The computer device 571 is capable of obtaining a CBCT scan obtained from the CBCT scanning unit 577 during scanning of a first and second body during movement and movement data of representing the movement of the respective first and second body obtained from the movement tracking unit 579. The obtained CBCT scan and movement data can be stored in the computer readable medium 572 and provided to the processor 573. The computer device 571 is programmed to reconstruct a first 3D model of the first body and a second 3D model of the second body by applying the recorded movement to the CBCT.

The CBCT scanner system comprises a computer keyboard 574 and computer mouse 575 for inputting parameters into the CBCT scanner system and the visual display unit 576 provides a visual interface where the user can verify data provided by the CBCT scanner system.

The CBCT scanner system also comprises a transmission unit 578 which allows data to be sent for further processing in other systems. For example, the transmission unit may be a connection to the internet via which the first and second 3D model of an upper and lower jaw respectively can be transmitted to a CAD/CAM implant planning software, such as Implant Studio by 3Shape, where a doctor may prepare implant planning, e.g. in order to provide implants for supporting dentures or other dental prostheses.

Although some embodiments have been described and shown in detail, the invention is not restricted to them, but may also be embodied in other ways within the scope of the subject matter defined in the following claims. In particular, it is to be understood that other embodiments may be utilized and structural and functional modifications may be made without departing from the scope of the present invention.

LITERATURE

[1] Charles L. Epstein. Introduction to the Mathematics of Medical Imaging, Second Edition. Siam 2008. ISBN: 978-0898716429.
[2] Jiang Hsieh. Computed Tomography; Principles, Design, Artifacts, and Recent Advances, Third Edition. SPIE 2015. ISBN: 978-1628418255

The invention claimed is:

1. A method for reconstructing at least a first and a second independently moving body from one 3D tomography scan data acquisition, comprising:
   performing a movement of the first body relative to the second body,
   obtaining a digital representation of the movement,
   obtaining a 3D tomography scan of the first body and the second body during the movement, and
   reconstructing a first 3D model of the first body and a second 3D model of the second body by applying the obtained movement to the 3D tomography scan.

2. The method according to claim 1, wherein obtaining the movement comprises recording the movement by attaching an at least first scan reference to the first body and tracking the at least first scan reference during the movement.

3. The method according to claim 2, wherein the method further comprises fixating the second body.

4. The method according to claim 2, wherein the method further comprises attaching a second scan reference to the second body and tracking the at least second scan reference during the movement.

5. The method according to claim 2, wherein a third or more bodies are present and a respective third or more scan references are attached to each third or more body and tracking each of the third or more scan references during the movement.

6. The method according to claim 2, wherein the movement is recorded by using an optical system comprising at least three cameras for detecting the one or more scan references.

7. The method according to claim 1, wherein the movement is digitized into a movement data file.

8. The method according to claim 7, wherein the movement data file is in a format compatible to the resolution of the 3D tomography scan.

9. The method according to claim 8, wherein the movement data from the movement data file is used in a reconstruction algorithm applied to the 3D tomography scan for reconstructing the at least first and second body.

10. The method according to claim 1, wherein the at least first and second body are considered rigidly moving bodies and that the movement of each body are represented by at least a first and a second transformation matrix.

11. The method according to claim 1, wherein the attenuation of each rigid body is described in a superposition of at least two linear models, each describing the attenuation of the respective at least first and second body.

12. The method according to claim 10, wherein the superposition of the at least two linear models are solved with respective at least first and second transformation matrix applied thereto.

13. The method according to claim 12, wherein the superposition of the at least two linear models is solved iteratively.

14. The method according to claim 12, wherein the superposition of the at least two linear models is solved non-iteratively.

15. A method for obtaining specific relative movement between at least a first and a second independently moving body, which has been reconstructed from one 3D tomography scan acquisition according to claim 1, comprising:
   performing a post movement of the first body relative to the second body after the 3D tomography data acquisition has been performed,
   obtaining the post movement.

16. A method according to claim 15, wherein an at least first scan reference attached to the first body is used to obtain the post movement.

17. A method according to claim 16, wherein the method further comprises a second scan reference attached to the second body use to obtain the post movement.

* * * * *